United States Patent [19]

Tusé et al.

[11] Patent Number: 5,262,381
[45] Date of Patent: Nov. 16, 1993

[54] METHOD TO ENHANCE INOCULATION OF ROOT SYSTEMS

[75] Inventors: Daniel Tusé, Fremont; Leslie Hokama, Mountain View; Jacqueline Tefft, Palo Alto; Gamin Wang, Menlo Park, all of Calif.

[73] Assignee: Osaka Gas Co. Ltd., Japan

[21] Appl. No.: 46,360

[22] Filed: Apr. 8, 1993

Related U.S. Application Data

[63] Continuation of Ser. No. 754,890, Sep. 6, 1991.

[51] Int. Cl.$^5$ ............................................. A01N 63/04
[52] U.S. Cl. ............................... 504/117; 71/DIG. 1
[58] Field of Search .................... 504/117; 71/DIG. 1

[56] References Cited

U.S. PATENT DOCUMENTS

| | | | |
|---|---|---|---|
| 4,434,231 | 2/1984 | Jung | 435/253 |
| 4,583,320 | 4/1986 | Redenbaugh | 47/58 |
| 4,755,468 | 7/1988 | Jung | 435/178 |
| 4,906,276 | 3/1990 | Hughes | 71/79 |
| 5,096,481 | 3/1992 | Sylvia et al. | 71/65 |

FOREIGN PATENT DOCUMENTS

| | | |
|---|---|---|
| 1945110 | 4/1970 | Fed. Rep. of Germany . |
| 54-117734 | 9/1979 | Japan . |
| 57-083230 | 5/1982 | Japan . |

OTHER PUBLICATIONS

*Sunset Magazine* "What about those new soil polymers?" reprint. pp. 1–3. Apr. 1987.
Nemec, *Trop. Agric.* (Trinidad) (1983) 60(2):97–101.
Menge, *Phytopathology* (1982) 72(8):1125–1132.
Nemec, *Can. J. Bot.* (1980) 58:522–526.
Johnsson et al., *J. Environ. Hort.* (1985) 3:166–168.
Beswetherick et al., *Trans. Br. Mycol. Soc.* (1987) 89(4):603–605.
Hwang et al., *Plant Disease* (1988) 72:448–452.
Groth et al., *Plant Disease* (1983) 67:1377–1378.
Strider, *Plant Disease Reporter* (1977) 61:746–748.
Leong, *Ann. Rev. Phytopathol.* (1986) 24:187–209.
Melero-Vara et al., *Plant Disease* (1982) 66:132–135.
Hamilton et al., *Tobacco International* (1982) 184:88–91.

*Primary Examiner*—Allen J. Robinson
*Assistant Examiner*—S. Mark Clardy
*Attorney, Agent, or Firm*—Morrison & Foerster

[57] ABSTRACT

Methods and compositions for effecting plant root infection with microorganisms, especially vesicular arbuscular mycorrhizal (VAM) fungi are disclosed. The method relies on a root baiting concept whereby the roots of a plant are caused to grow towards and/or through a material which contains an inoculum of the microorganism. Typically bead-like materials are produced which are comprised of (1) a bait material for which roots have a natural affinity; (2) an inoculum of a microorganism which can infect plant roots and improve their growth and/or health; and (3) a carrier material that supports and localizes the bait and the inoculum. The bait may be water or another suitable material such as a plant growth regulator and the carrier is typically a non-phytotoxic crosslinked polymer especially a water absorbing polymer. The compositions are placed in the vicinity of the plant roots. The bait draws the roots towards the composition to permit infection of the roots with the microorganism.

13 Claims, No Drawings

METHOD TO ENHANCE INOCULATION OF ROOT SYSTEMS

This application is a continuation of application Ser. No. 07/754,890, filed Sep. 6, 1991.

FIELD OF THE INVENTION

The present invention is directed to a means of enhancing the growth of plants by treating root systems. More particularly, the present invention is directed to a method of directing plant root growth so as to promote the infection or colonization of plant root-derived material by beneficial microorganisms.

BACKGROUND OF THE INVENTION

A number of microorganisms are known which are beneficial in plants. For example, vesicular arbuscular mycorrhizal (VAM) fungi are microorganisms found in soil which enter into a beneficial symbiotic relationship with many plants. These fungi aid the host plant in obtaining nutrients, particularly phosphorous, from the soil, and appear to confer resistance to plant pathogens. Many of the crops capable of forming beneficial symbiotic relationships with VAM fungi are susceptible to common pathogenic fungi found in the rhizosphere.

A typical way of treating soil infected with pathogenic fungi or other pathogens is to treat the field in its entirety with a fungicide or fumigants. This procedure is most relevant when it is unclear that the soil organisms present are appropriate for the intended crop, such as in areas of crop rotation, reclamation of nonagricultural land, e.g., pollution sites, mine spills or sand dunes and in other areas where rapid establishment of crops is needed. The most common techniques of fumigation, with agents such as methyl bromide, eliminate beneficial microorganisms as well as the plant pathogens. Therefore, reinoculation with beneficial microorganisms is of special importance in aiding recolonization and crop growth as well as preventing reestablishment of undesired microbes.

Using VAM infection as an illustration, various methods of effecting beneficial infection by VAM fungi have been disclosed. For example, Nemec, *Trop Agric* (Trinidad) (1983) 60:97-101 describes the inoculation of citrus seedlings by dipping plant roots in an inoculum comprised of VAM fungi and a sticking agent, and the effect of various fumigants and fungicides on VAM fungi has been studied. See, e.g., Menge, *Phytopathology* (1982) 72:1125-1132; Nemec, *Can J Bot* (1980) 58:522-526. In addition, Johnson, C. R. et al., *J Environ Hort* (1985) 3:166-168 report the use of hydrophilic polymers as carriers for VAM inocula. In their experiments, four methods of inoculation were used: mixing the inoculum into the soil of potted plants; placing the inoculum directly beneath the root system of the cutting; dipping the root system into a slurry of "Terrasorb", a commercially available polymer manufactured by Industrial Services International, Bradenton, Fla., at 1.5 g/100 mL water; and dipping the root system into a slurry of Viterra plant gel, manufactured by Nepera Chemical Company, Harriman, N.Y., at 1 g/100 mL water. The particular polymers and dipping protocols used in the Johnson article are said to have resulted in lower inoculation levels than the alternative processes known in the art. In addition, the article by Beswetherick, J. T. et al., *Trans Br Mycol Soc* (1987) 89:603-605 describes the inoculation of roots with VAM by sandwiching the roots between squares of cellophane to which the fungal mycelium has been attached and references a number of other techniques for inoculation.

Hwang, *Plant Disease* (1988) 72:448-452, describes the treatment of seeds with the fungicide metalaxyl followed by planting in soil inoculated with a VAM fungus. Groth et al., *Plant Disease* (1983) 67:1377-1378, describes the effect on plant growth of using soil treated with both metalaxyl and VAM fungi. Strider, *Plant Disease Reporter* (1977) 61:746-748, describes the use of benomyl in a root dip to help control Rhizoctonia root rot. German Democratic Republic Patent No. 128,396 (1977), is directed to method of controlling root diseases of cereals by coating the seeds with a nutrient substrate for antagonistic microflora and a fungicide. Leong, *Ann Rev Phytopathol* (1986) 24:187-209, is a review of the role of siderophores in the biocontrol of plant pathogens. Melero-Vara et al., *Plant Disease* (1982) 66:132-135, is directed to a seed dressing containing metalaxyl to control downy mildew.

It is also known to coat the roots of seedlings during transplantation with a polymeric material to, for example, prevent desiccation. See, e.g., Hamilton et al., *Tobacco International* (1982) 184:88-91; Federal Republic of Germany Patent No. 1,945,110 (1970); Japanese Patent No. 57/083230 (1982); Japanese Patent No. 54/117734 (1979). In addition, U.S. Pat. Nos. 4,434,231 and 4,755,468, both to Jung, disclose crosslinking of polymer vehicles used to coat root systems by various means. Crosslinking, however, may suppress spore germination and infection.

There are currently at least four known methods of enhancing the infection of plant roots with beneficial microbial cultures also known as live soil inoculants. These methods include broadcasting, banding, layering and root coating. The broadcasting methodology relies on a "shotgun" approach of inoculation whereby pellets of inocula are disseminated over large areas of soil with no control over how much of the inocula will reach the rhizosphere and ultimately lead to root infection. Banding involves a methodology whereby lines or "bands" of inocula are alternated with rows of plants. Inoculation of the roots with the microbes and the banded inocula takes place as the plant roots grow and spread through the lines or bands containing the inocula. The method does not provide any control with respect to root infection and is merely facilitated by the positioning of o the inocula and the plants in bands or lines. Layering is a technique whereby layers of inocula are placed beneath the roots of seedlings. This methodology works in a manner similar to that of "banding" in that the roots of the plants become infected by the microbes as the roots grow downward and through the layer of inocula. Thus, layering is similar to banding in that it does not control the efficiency of root infection. Lastly, root coating is a technique which increases the efficiency of the delivery of inocula to the roots by placing the roots in close contact with the inocula via coating. However, the methodology requires that precautions against root damage and contamination be taken, thus, increasing the level of effort required to carry out the procedure.

As indicated above, there are techniques available which attempt to enhance the degree of infection of plant roots by beneficial microorganisms. However, such methods suffer from a number of disadvantages. Accordingly, there continues to exist a need for an improved economical and efficient method for enhancing the degree of root infection with beneficial microbes. The present invention provides such a method.

DISCLOSURE OF THE INVENTION

The invention is directed to compositions and methods which effect the infection of plants, in particular plant roots, with beneficial microorganisms which are helpful in enhancing growth or preventing disease. The compositions employ attractants which cause the roots to grow in their direction. As the inoculum of the microorganisms are supplied in conjunction with the location of the bait material, the presence of the attractant permits efficient infection of the roots.

The efficiency permitted by the invention method is particularly important with respect to inocula such as VAM fungi wherein the inoculating cultures are difficult and expensive to prepare. VAM fungi are symbiotic and cannot be cultivated in pure culture. They require the presence of plant root-derived material for their normal development, and thus the production of propagules is expensive and labor intensive. Because the invention method operates to attract the roots of the plant to be infected, lower concentrations of propagules can be used. While prior art methods, which rely on chance contact between the propagules and plant roots or uniformly coat the plant root with a preparation containing the propagules, require large amounts of inoculum, the invention method permits more efficient and effective inoculation, thus reducing cost and eliminating unnecessary quantities of inoculum.

Thus, in one aspect, the invention is directed to compositions useful in infecting plant roots with beneficial microorganisms. The compositions comprise a carrier to which is coupled or attached both the inoculum which provides the microorganisms for infection and with a bait material which is an attractant for the root. The compositions are generally such that the inoculum is localized. One such strategy is to use compositions which are particulate wherein the particulate carrier localizes the inoculum and bait. Other embodiments of the invention composition include sponges or slurries which serve to localize the two essential components. The compositions may also contain a binder to enhance or stabilize the coupling of the inoculum and/or bait to the carrier.

Specifically, in this respect the invention is directed to a composition for effecting the infection of plant roots with a microorganism, said composition comprising:

(a) an inoculum of the microorganism capable of infection of plant roots;

(b) a bait material for which roots have a natural affinity; and (c) a non-phytotoxic polymeric carrier for said microorganism and bait material. The carrier should exhibit little or no toxicity to the microorganism within a practical range of carrier concentration.

In another aspect, the invention is directed to a method to infect roots with beneficial microorganisms which comprises placing the localized compositions of the invention in locations relative to the plants which permits the growth of the roots toward the locations of the compositions so that infection can be effected. Specifically, the invention is directed to a method of effecting the infection of plant roots with an inoculum of a microorganism which method comprises providing the composition of claim 1 in a position relative to said plant roots whereby said plant roots can be attracted, and more specifically to a method to introduce a growth promoting VAM infection into the roots of a plant which comprises placing in a position wherein it is possible that the roots of said plant would be able to grow, a composition comprising VAM propagules attached to a carrier containing water as an attractant so as to cause the roots to grow toward the composition, contact the composition, and thereby infect the roots with VAM.

Described below are detailed conditions for preparation of the composition herein defined, procedures for the use of this composition, and its method of application to plants.

MODES OF CARRYING OUT THE INVENTION

The invention provides compositions which are effective in infecting plant roots with beneficial microorganisms. The compositions are macroscopic localized formulations comprised of a carrier which forms the body of the formulation, a bait material which is a natural attractant for roots, and an inoculum of the microorganism coupled thereto. A binder may also be included to prevent decoupling of the various components of the system.

The physical form of the carrier may be as a particulate, film, sponge, slurry, viscous solution or the like, so that a localized concentration of the bait and inoculum is established, thus creating a diffusion gradient of the bait toward the targeted plant root system. The carrier is typically a crosslinked polymer which is biocompatible and has limited biodegradability. However, the polymer need not be synthetic, but can include natural materials such as silica gel or clay. It need only support the bait material and inoculum and permit formation of a gradient. The carrier can preferably be sterilizable and resistant to mechanical breakdown and capable of providing particles of relatively uniform size if desired. It is also advantageous that the carrier be relatively economical and compatible with the materials that are used in the production of the final product.

The requirement for biocompatibility discourages the use of toxic crosslinking agents, and hence preferred polymers include polyacrylamide, insoluble polysaccharides, such as grafted starch, and various hydrogels used in medicine and pharmacy, such as those described by Peppas, N. A. "Hydrogels in Medicine and Pharmacy" (1986) CRC Press, Boca Raton, Fla. In general, the hydrogels include the hydrophilic polymers of methacrylates, such as hydroxyethyl methacrylate (HEMA), hydroxyethyoxyethyl methacrylate (HEEMA), hydroxydiethoxyethyl methacrylate (HDEEMA), methoxyethyl methacrylate (MEMA), methoxyethoxyethyl methacrylate (MEEMA), methoxydiethoxyethyl methacrylate (MDEEMA), ethylene glycol dimethacrylate (EGDMA), as well as other polymers, such as N-vinyl-2-pyrrolidone (NVP), methacrylic acid (MA), vinyl acetate (VAc), acrylamide (AA), and propylene glycol monoacrylate (PGMA).

The polymers of these monomers and the polymers listed above are especially useful in embodiments wherein the attractant is water as they are capable of swelling to many times their weight when treated with water. For example, Super Slurper ™, a grafted starch, can absorb up to 2,000 times its weight in water; Broadleaf P4 ®, which is a polyacrylamide, can absorb 500 times its weight in water. Polymers of the foregoing monomers also absorb large amounts of water. In general, when water is used as bait material, water will comprise about 75-99%, preferably 75-95% (wt/wt) of the compositions of the invention as employed under typical field conditions.

Additional amounts of water can be used in the preparation of the compositions of the invention, however, and the percentage of water during the preparation is dependent on convenience in handling. The compositions as prepared can subsequently be dried down for packaging, storage and shipping. Under these conditions, the formulated compositions are approximately 25-50% (wt/wt) of water in many cases. The stored product is then rehydrated to the above desired level for use.

The level of water entrapped in the polymer can be controlled by selection of the monomer and the amount of crosslinking; of course, copolymers can also be used.

Methods of producing hydrogels have been investigated by Refojo, M. F. et al. *J App Polym Sci* (1965) 9:2425-2435, who showed that by wet crosslinking, hydrogels maintain their original shape and volume fairly well compared with dry crosslink polymer networks. The maximum amount of water which can be maintained in transparent hydrogels depends on the hydrophilicity of the monomers and ranges from about 40% for PGMA and/or HEMA gels when transparent to about 600% for the same monomer when opaque.

In addition, a hydrogel structure can be obtained using radiation polymerization as described by Kumakura, M., et al., *J Material Sci* (1984) 19:1616-1621. The pore size can be varied with the polymerization conditions as described. An additional method for formation of support is described by Haldon, R. A., et al., *Brit Polym J* (1972) 4:491-501. The formation of a support is advantageous in retaining the inoculum. Alternative methods are described by Foss, C. R., et al., "Proc. 7th Int. Cong. Plant Tissue and Cell Culture," Amsterdam, The Netherlands, 1990.

Although the invention is illustrated herein by the use of water as a bait, and this is a highly convenient method, especially in dry soils, alternative attractants can also be used. For example, plant growth regulators such as auxins, cytokinins and giberellins may also be used as bait material and may be advantageous in wet soil. As used herein, "plant growth regulator" refers to a substance that interacts with plants or their tissues, organs or cells so as to modify gene expression, metabolism, growth, composition, morphology or ontogeny of the plant or its components. In this case, selection of a polymer which will effect adsorption of the hormone may be desirable to slow the diffusion of the hormone into the soil as an attractant.

The inoculum comprises propagules, i.e., live cultures, spores, hyphae, infected root-derived materials, etc., of the desired microorganisms. Root-derived materials include root tissue, hair cells, tips, coarse or fine structural elements, and can be derived from adventitious lateral roots as well as tap roots. These microorganisms, in general, include fungi and bacteria. Bacteria useful as inocula in the positions and methods of the invention include Rhizobium, Azotobacter, Frankia, or other nitrogen fixing bacteria; Pseudomonas, *Bacillus thuringiensis*, or other bacteria that produce antibiotic substances or responses; and various Bacillus and other species which are phosphate-solubilizing bacteria, and other symbionts. Suitable fungi include the ectomycorrhizae; the endomycorrhizae, the Trichoderma or other fungi which produce antibiotic substances, and additional symbiotic fungi. The vesicular arbuscular mycorrhizae (VAM) which are used to illustrate the invention herein, and which are a preferred embodiment, are endomycorrhizae.

VAM fungi are also known in the art as VA mycorrhizal fungi. Many VAM genera have been identified, including Acaulospora, Sclerocystis, Gigaspora, Scutellispora, Glomus and Entrophospora. Particularly important VAM genera are Gigaspora, Scutellispora, and Glomus. Examples of Glomus species include, but are not limited to, *G. intraradices, G. etunicatum, G. mosseae, G. fasciculatum, G. deserticola, G. macrocarpum, G. microcarpum, G. constrictum, G. occultum* and *G. clarum*. Examples of Gigaspora species include, but are not limited to, *G. margarita, G. gigantea, G. decipiens*, and *G. albida*. Examples of Scutellispora species include, but are not limited to, *S. gregaria, S. calospora, S. nigra* and *S. pellusida*. (See N. C. Schenck & Yvonne Perez, *Manual for the Identification of VA Mycorrhizal Fungi* (1990) 3rd Ed.)

"VAM propagules" refers to any infectious agent or composition capable of inducing VAM infection in plant roots. Thus, VAM propagules can include, but are not limited to, VAM spores, VAM hyphae, VAM hyphal tips, and VAM-infected root-derived material.

The inoculum contained on the carrier is in general a "propagule" of the infectious agent, and can similarly include the microorganisms themselves, spores, hyphae and infected root-derived material as is appropriate for the microorganism concerned. It may be necessary to supply a binding agent such as, for example, polyvinyl pyrrolidone (PVP), polyvinyl alcohol (PVA), methyl cellulose, or hydroxypropyl methylcellulose to couple the inoculum to the carrier. Polyacrylamide can also serve as a binding agent, as well as a carrier.

Preparation of Invention Compositions

The invention compositions are solid or semisolid supports wherein a carrier is coupled or bound both to a natural attractant and a suitable inoculum. In typical particulate formulations, the dehydrated particles are 0.5-2.5 mm in diameter prior to hydration. A binding agent may also be supplied. In addition to particulate formulations, the solid or semisolid supports can be supplied in the form of sponge-like polymers, films, or smaller particulates which can be formulated as slurries or viscous polymer solutions. In any case, for instances wherein water is used as bait, a polymer capable of forming a hydrogel is wetted and allowed to absorb water to swell to a volume at least several times its original size. Although the hydrophilic carriers can absorb 500-2,000 times their weight in water, a practical range for the applications in the final composition is substantially less--about 10 times their weight in water.

As set forth above, during the preparation stage, arbitrary amounts of water are included for ease of handling. The composition can, if desired, be stored in a relatively dry form having, for example, in the range of 25-50% (wt/wt) of water. In use in the field, however, the compositions are rehydrated if necessary to obtain water contents of 70-99%, preferably 75-95% water, when water is to be used as bait.

The inoculum is coated on the surface of the particles or included in the slurry, sponge, or film either before or after (or during) the swelling. The inoculant can be coated directly or coupled with a binding agent such as those described above.

The quantity of inoculum required varies depending on the nature of the microorganism, but for most species of VAM, the amount of propagule generally can range from 2,000-20,000 spores per g dry weight of carrier. However, the distribution of the spores is concentrated at the situs of the carrier so that the overall number of spores or propagules required for a given series of plants is greatly reduced. For each microorganism, however, an appropriate level of concentration can be optimized.

An illustrative composition might include, for example, a mixture of 4 gm of polyacrylamide beads as carrier, 8 ml of about 0.5-2.5% w/v polyvinyl alcohol solution as binder and about 75,000 VAM spores, mixed in 28 ml of water. The water is required in this preparation in order to obtain uniform coating. The resulting coated beads, obtained by mixing the foregoing, can then be dried to about 25-50% (wt/wt) moisture and rehydrated previous to or after placement in the soil. This quantity was sufficient to treat 18-20 five-gallon containers and could also be used to treat 80-100 gallons of soil. Once rehydrated, the water is slowly released into the soil forming a gradient so as to act as an attractant for the roots. However, using single plants per container, more inoculum may be needed to effect infection. With higher planting densities, less inoculum may be used because the extra root surface area available will increase the probability of contact between the inoculum and root-derived material for the propagation of infection. Also, less inoculum may be needed under more conventional nursery/agronomic practices. In the illustrative inoculation below, extreme conditions were used to demonstrate baiting, including severe limitations and large separation between the plant and the inoculum.

In another, direct approach, a suspension of the VAM propagules or other microorganism culture is added to the wet polymer by any convenient methodology. A suitable number of propagules or cells is used; this can be determined experimentally. It has been found that, in the illustrated procedure below, about 100 spores or propagules per cubic cm of bead material can be effective, and concentrations of approximately 500 or more spores per cubic cm can also be used. The propagules can be applied in concentrated zones or can be evenly dispersed in or on the beads. Any convenient geometry can be employed depending on the form of the polymeric delivery system. The polymeric beads can be allowed to dry until the moisture content is relatively low, for example for 72 hours at 20°-30° C. If the propagules are present in the beads in higher amounts, then smaller numbers of them can be distributed to obtain the desired results of root infection.

In general, the ratios of the components of the compositions of the invention will vary according to the nature of the carrier, the nature of the bait, and the nature of the inoculum. In general, if the bait material is water, the composition, when placed in use under typical field conditions, will be 75-99%, preferably 75-95% (wt/wt) water. On the other hand, if the bait is a plant growth regulator, amounts smaller than the amount of carrier can be used. The amount of inoculum depends on the nature of the microorganism; as stated above, for VAM fungi, inocula of about 2,000-20,000 spores/g dry carrier are used in the preparation of the compositions.

It is clear that the ratios and proportions of the three components of the system will be dependent on the natures of these components and the manner of application of the compositions to plant root systems. Determination of optimum ratios is clearly within ordinary optimization procedures.

Additional Materials

In addition to the bait, inoculant and carrier, formulations of the invention may include materials which confer desirable properties to complement infection. For example, insecticides or herbicides directed to other plants might be added.

Plant growth adjuvants can also be used. Examples of such adjuvants include growth regulators, such as ascorbic acid (AA), gibberellic acid (GA) and indoleacetic acid (IAA) [see, e.g., Patil et al., *Indian J Plant Physiol* (1981) 24:145-149], or microorganisms with the ability to solubilize mineral phosphates. See, e.g., Goldstein, *Amer J Alternative Agriculture* (1986) 1:51-57; Shingte et al., *J Maharashtra Agric Univ* (1987) 12:121-122. Other materials known to those skilled in the art and generally used in the field of agriculture to promote plant growth can also be used.

Additional components used in the invention compositions can also be any agent, including a chemical or biological agent, that selectively inhibits the infection or growth of a plant pathogen or fungus relative to the desired microorganism, particularly in the root zone, when formulated into the bead forming compositions at an effective concentration. The identification of chemical agents that selectively inhibit root pathogens, such as *Pythium spp., Rhizoctonia spp., Phytophthora spp.*, or *Fusarium spp.*, is known in the art. See, e.g., Menge, *Phytopathology* (1982) 72:1125-1132. Particularly preferred chemical fungicides are aluminum tris(-O-ethyl phosphonate) [fosetyl Al; Aliette ®], and N-(2,6-dimethylphenyl)-N-(methoxyacetyl)-alanine methyl ester [metalaxyl; Ridomil ®]. VAM fungi are not affected by these fungicides. Some chemical fungicides may be selective only at reduced concentrations, such as captan. See, e.g., Nemec, *Can J Bot* (1980) 58:522-526; Sutton et al., *Can J Bot* (1976) 54:326-333.

Biological pesticides comprise any organisms, such as bacteria, fungi, or viruses, that provide for the selective inhibition of pathogens relative to the desired or beneficial microorganisms when included in the root coating compositions of the present invention. The selective inhibition can be induced either directly (e.g., toxicity to fungal pathogen), or indirectly (e.g., competition, inducing plant immunity, etc.). Particularly preferred biological fungicides are microorganisms such as bacteria that produce siderophores. Such bacteria are well known in the art. See, e.g., Leong, *Ann Rev Phytopathol* (1986) 24:187-209; Gill et al., *J Bacteriol* (1988) 170:163-170; Buyer et al., *J Biol Chem* (1986) 261:791-794; and deWeger et al., *J Bacteriol* (1986) 165:585-594. Particularly preferred are growth-promoting *Pseudomonas spp*. Fungicidal strains are typically of the *Pseudomonas fluorescens-Pseudomonas putida* group that rapidly colonize plant roots and cause statistically significant increases in plant yield. See, e.g., Schroth et al., *Science* (1982) 216:1376-1381. Suitable strains of Pseudomonas isolated from the rhizosphere can be identified by screening for fungal inhibition. See, e.g., Gill et al. (1988), supra. Suitable Pseudomonas strains are also available commercially (e.g., Dagger G ®; Ecogen Inc., Langhorne, Pa.).

Method of Application

The particulate carriers of the invention bearing the inoculum and bait are typically in the form of "beads"

as described above. In applying the compositions, the beads are buried around the roots of a seedling. In general, the beads are supplied in those locations which can readily be accessed by the roots under the influence of the attractant. The plants are supplied as seeds, seedlings, cuttings or established plants.

The methods and formulations of the present invention have applicability to a wide variety of plants. Particular plant/microorganism relationships are taken account of. It appears that VAM fungi, for example, can colonize the roots of over 90% of all plants. The present invention will have particular application in economically important agronomic and horticultural crops which are subjected to transplantation. Table 1 lists representative crops which can benefit from VAM colonization, such as that provided by the present invention.

TABLE I

Crops Colonized by VAM

Fruit and Nut Crops:

| | | |
|---|---|---|
| Almond | Date Palm | Pear |
| Apple | Fig | Pecan |
| Apricot | Grape | Pineapple |
| Avocado | Kiwi | Pistachio |
| Blackberry | Melon, All | Raspberry |
| Cherry | Olive | Strawberry |
| Citrus, All | Papaya | Walnut |
| Currant | Peach | |

Vegetable Crops:

| | | |
|---|---|---|
| Artichoke | Cucumber | Pepper, All |
| Asparagus | Eggplant | Potato |
| Beans, All | Garlic | Squash |
| Carrot | Lettuce | Tomato |
| Cassava | Okra | Yam |
| Celery | Onion | |

Agronomic Crops:

| | | |
|---|---|---|
| Alfalfa | Cotton | Soybean |
| Cereal Grains | Peanut | Sunflower |
| Clover | Rice | Wheat |
| Corn | Tobacco | |

Ornamental Crops

| | | |
|---|---|---|
| Agapanthus | Boxwood | Cedar |
| Araucaria | Carrisa | Cotoneaster |
| Barberry | Ceanothus | Cupressus |
| Dogwood | Liriodendron | Russian Olive |
| Fern | Mahonia | Sweet Gum |
| Forsythia | Maples, All | Sycamore |
| Gardenia | Palms | Taxus |
| Green Ash | Photinia | Viburnum |
| Holly | Pittosporum | Vinca |
| Juniper | Podocarpus | Xylosma |
| Ligustrum | Raphiolepis | Boston fern |
| Staghorn ferns | | |

Flower Crops:

| | | |
|---|---|---|
| Chrysanthemum | Bulbs, All | Fuchsia |
| Petunia | Roses, All | Morning Glory |
| Marigold | Snap Dragons | Nasturtium |
| Begonia | Impatiens | Geranium |

The following is a list of specific plant species which are often transplanted and can benefit from the application of the methods and formulations of the present invention:

*Cucumis spp.* (melon)
*Vitis spp.* (grapes)
*Apium spp.* (celery)
*Fragaria spp.* (strawberry)
*Citrus spp.* (orange, lemon, lime, etc.)
*Camellia spp.* (e.g., *C. sinensis*; tea)
*Solanum spp.* (e.g., *Nicotiana tabaccum* tobacco)
*Oryza spp.* (rice)
*Begonia spp.* (Begonia rex)
*Lycopersicon spp.* (tomato)

-continued

*Asparagus spp.* (asparagus)
*Cynara spp.* (artichoke)
*Nephrolepis spp.* (e.g., *N. exaltata*; Boston fern)
*Davallia spp.* (ferns)
*Platycerium spp.* (staghorn ferns)
*Malus spp.* (apple)
*Prunus spp.* (e.g., *P. avium*; sweet cherry)
*Rubus spp.* (e.g., *R. idaeus*, raspberry; *R. laciniatus*, blackberry)
*Pyrus spp.* (pear)
*Carya spp.* (e.g., *C. illinoinensis*; pecan)
*Allium spp.* (onion)
*Gossypium spp.* (cotton)
*Tulbaghia spp.* (agapanthus)
*Buxus spp.* (boxwood)
*Cedrus spp.* (cedar)
*Cornus spp.* (dogwood)
*Acer spp.* (maple)
*Areca spp.* (palm)
*Phoenix spp.* (palm)
*Pittosporum spp.* (pittosporum)
*Rosa spp.* (rose)
*Chrysanthemum spp.* (chrysanthemum)

As stated above and illustrated below, the compositions of the invention are included in the soil so as to create a gradient to effect the attraction of the roots toward the invention compositions. The amounts of composition required depend on the nature of the plant, the nature of the inoculum, the nature of the bait material, and the integrity of the carrier. Optimum amounts of composition for particular growth situations can readily be determined by simple optimization experiments.

The following examples are intended to illustrate but not to limit the invention. Unless indicated otherwise, parts are parts by weight, temperatures are in degrees centigrade, and pressure is at or near atmospheric.

EXAMPLE 1

Effect of Hydrobaiting on Soybeans

An inoculum of the VAM species *Glomus mosseae* was prepared by wet-sieving 1 liter of mother culture soil containing VAM infected roots, fungal hyphae, and spores followed by centrifuging in a sucrose gradient. The resulting inoculum, which contains spores, hyphae, and some infected root-derived material, was resuspended in 20 ml water (sufficient volume for uniform coating) and 7 ml of 2.5% (w/v) polyvinyl alcohol was added and mixed. The mixture was added to 4 gm polyacrylamide beads (e.g., Broadleaf P4 ®) and the mixture was allowed to dry at room temperature for 24 hr. This inoculum is sufficient for eight test pots.

Control inocula were prepared consisting of 120 ml aliquots of the soil from the same mother culture as that used to prepare the P4 carrier-based inoculum. Each 120 ml inoculum aliquot was sufficient for one pot.

Soybean seeds (Ransom Cultivar) were planted about 4 cm from the edges of 20 liter pots in a mixture of Balcom (clay) soil:sand, 1:4. The inoculum treatments to be tested were placed approximately 18 cm from the plant in a column extending from 2 cm below the surface to approximately 12 cm below the surface. Eight replicate pots were used for each treatment or inoculum to be tested. These treatments were: 1) the test hydrobait inoculum prepared above; 2) the inoculum control (inoculum only, mother culture soil); 3) a hydrogel control without inoculum (hydrogel only); and 4) plant control (no inoculum or hydrogel).

The seeds were watered daily until the plants were established and the plants were then thinned to one plant per pot. Then 50 ml of water was supplied per pot every other day directly over the hydrobait or inoculum control location. After 12 weeks the soybeans were harvested and the root growth was examined. Plant tissues were weighed and root subsamples were taken to determine infection.

Visual observation confirmed that the moisture gradient in pots containing the P4 hydrobait was well distributed across the width of the pot within the range of the inoculum column.

VAM infection when control inoculum was used was inconsistent and ranged from 0–21.5%. Infection in the hydrobait inoculum pots ranged from 10.5–41.4%. A summary of the average results of infection and growth is shown in Tables 2 and 3.

TABLE 2

Effect of P4 Beads on VAM Infection, Total Infected Root Length, and Soil Moisture Content

| Treatment | Percent Infection | Infected Root Length (cm) | Moisture Content in Soil (%) |
|---|---|---|---|
| Plant only | n.a. | n.a. | 1.3 |
| Inoculum only | 9.4 | 188 B | 3.2 |
| Hydrogel only | n.a. | n.a. | 13.8 |
| Hydrobait inoculum | 28.3 | 977 A | 15.5 | na = not applicable

TABLE 3

Effect of P4 Beads and VAM on Plant Growth

| Treatment | Plant Height (cm) | Shoot Dry Weight (g) | Root Dry Weight (g) | Root Length (cm) |
|---|---|---|---|---|
| Plant only | 15.5 C | 0.53 C | 0.65 B | 1149 B |
| Inoculum only | 18.3 H | 0.74 BC | 0.93 B | 1823 B |
| Hydrogel only | 16.1 BC | 0.99 B | 0.90 B | 1283 B |
| Hydrobait inoculum | 26.3 A | 2.25 A | 1.52 A | 3224 A |

The results in Tables 2 and 3 demonstrate that the use of the hydrobait inoculum at 0.4 gm/pot show more efficient infection (i.e., percent infection and infected root length, Table 2) than a comparable amount of inoculum only, with a resulting increase in total root length, and growth in general (Table 3). Statistical differences in the results were determined using Duncan's Multiple Range Test. This test is used for determining differences between all possible pairs of treatment means. Those treatments with the same alphabet notation (A, B, C) are not significantly different and those with different letters are significantly different ($p < 0.05$). Results show that those plants treated with the hydrobait inoculum were significantly larger and contained a higher VAM colonization than the various controls.

Hydrobait-treated roots were thicker, possibly due to improved turgor, than the roots of the untreated plants; it was also observed that the leaves of plants treated with the hydrobait inoculum were greener and thicker than any of the controls, and that the roots visibly grew toward the hydrobait. The roots were most dense in the high water content region of the gradient. An abundance of fine roots was observed passing through the hydrobaited inoculum.

It is recognized that the nutrient and water stress conditions of this experiment which were imposed to demonstrate the hydrobaiting concept resulted in deleterious effects on the untreated plants. The inoculum and hydrogel controls provided some compensation for this stress. However, when the hydrobait inoculum was used, the beneficial effects were greatly enhanced and synergistic.

EXAMPLE 2

Effect of Hydrobait Inoculum on Corn

Hydrobaited inoculum was prepared exactly as described in Example 1 except that the mixture of polyacrylamide beads with the binding agent/inoculum mixture was dried more slowly. The mixture was placed in a closed container with small holes to protract drying to a 10% moisture content to 72 hr, and mixtures of varying concentrations of mother culture were used. The control inoculum using the higher concentration of 120 ml fresh soil was prepared as in Example 1.

Plants were grown as described in Example 1, except that seeds of corn (*Zea maize*) were used and the soil pH was controlled to neutrality with calcium hydroxide. The culture protocol was as described in Example 1, and the plants were harvested and analyzed after 11 weeks, The results are set forth in Table 4.

TABLE 4

| Treatment | Plant Height (cm) | Total Dry Weight (g) | Total Root Length (cm) | Percent Infection | Infected Root Length (cm) |
|---|---|---|---|---|---|
| Plant only | 42 | 1.35 | 906 | 0 | 0 |
| Inoculum only-2 | 41 | 1.25 | 860 | 0 | 0 |
| Hydrobait inoculum-1 | 57 | 3.34 | 2663 | 21 | 559 |
| Hydrobait inoculum-2 | 65 | 2.16 | 1289 | 18 | 232 |

As shown in Table 4, use of the hydrobait inoculum greatly improved the infection in growth of the plants. The inoculum control was under sufficient stress due to the watering protocol that no infection occurred. However, the hydrobait inoculum-1 (which contained inoculum derived from 60 ml of soil) resulted in infection, as did the hydrobait inoculum-2 pots (which contained inoculum from 120 ml of soil).

We claim:

1. A method of effecting the infection of plant roots with an inoculum of a microorganism, which method comprises providing a composition comprising
   (a) an inoculum of the microorganism capable of infection of plant roots;
   (b) a bait material for which roots have a natural affinity; and
   (c) a non-phytotoxic polymeric carrier for said microorganism and bait material;
in a position distal to said plant roots, and relative to said plant roots whereby said plant roots can be attracted to said composition.

2. The method of claim 1 wherein said plant is selected from the group consisting of: *Malus spp., Prunus spp., Fragaria spp., Rubus spp., Pyrus spp., Carya spp., Apium spp., Allium spp., Gossypium spp., Tulbaghia spp., Buxus spp., Cedrus spp., Cornus spp., Acer spp., Areca spp., Phoenix spp., Pittosporum spp., Rosa spp., Citrus spp., Vitis spp., Camellia spp., Cucumis spp.,* and *Chrysanthemum spp.*

3. The method of claim 1 wherein said plant is a seed, seedling, cutting, or established plant.

4. The method of claim 1 wherein the microorganism is a VAM propagule.

5. The method of claim 4 wherein said VAM propagule is selected from the group consisting of Gigaspora, Glomus and Scutellispora.

6. The method of claim 1 wherein the carrier is in the form of a particulate, sponge, slurry, viscous solution, or film.

7. The method of claim 1 wherein the bait material is water and wherein said carrier is capable of absorbing water so that water comprises at least 75% by weight of said composition.

8. A method to introduce a growth promoting VAM infection into the roots of a plant which comprises placing in the vicinity of the roots of said plant, a composition comprising VAM propagules attached to a carrier containing water as an attractant so as to cause the roots to grow toward the composition, contact the composition, and thereby infect the roots with VAM.

9. The method of claim 8 wherein said plant is selected from the group consisting of: *Malus spp., Prunus spp., Fragaria spp., Rubus spp., Pyrus spp., Carya spp., Apium spp., Allium spp., Gossypium spp., Tulbaghia spp., Buxus spp., Cedrus spp., Cornus spp., Acer spp., Areca spp., Phoenix spp., Pittosporum spp., Rosa spp., Citrus spp., Vitis spp., Camellia spp., Cucumis spp.,* and *Chrysanthemum spp.*

10. The method of claim 8 wherein said plant is a seed, seedling, cutting, or established plant.

11. The method of claim 8 wherein said VAM propagule is selected from the group consisting of Gigaspora, Glomus and Scutellispora.

12. The method of claim 8 wherein the carrier is in the form of a particulate, sponge, slurry, viscous solution, or film.

13. The method of claim 8 wherein said carrier is capable of absorbing water so that water comprises at least 75% by weight of said composition.

* * * * *